United States Patent [19]
Arndt et al.

[11] Patent Number: 4,975,107
[45] Date of Patent: Dec. 4, 1990

[54] SOIL TREATING METHOD AND COMPOSITION FOR CONSERVING NITROGEN IN NATURALLY ALKALINE SOIL

[75] Inventors: Kim E. Arndt, Pittsburg; Ronald W. McCormick, Concord, both of Calif.

[73] Assignee: The Dow Chemical Company, Midland, Mich.

[21] Appl. No.: 823,566

[22] Filed: Jan. 29, 1986

[51] Int. Cl.[5] .................... C05G 3/08; C07D 231/10
[52] U.S. Cl. .......................................... 71/11; 71/27; 71/90 Z; 548/377; 548/378
[58] Field of Search ................... 71/7, 90 Z, 11, 27; 548/377, 378

[56] References Cited

U.S. PATENT DOCUMENTS

| 3,135,594 | 6/1964 | Goring | 71/11 |
| 3,494,757 | 2/1970 | Osborne | 71/1 |
| 3,635,690 | 1/1972 | Griffith | 71/1 |

FOREIGN PATENT DOCUMENTS

| 0222471 | 5/1985 | Fed. Rep. of Germany | 71/7 |
| 1592516 | 7/1981 | United Kingdom . | |

Primary Examiner—Ferris H. Lander
Attorney, Agent, or Firm—S. Preston Jones; Ronald G. Brookens

[57] ABSTRACT

4-Fluoro-3-methylpyrazole is employed to obtain prolonged nitrification inhibition in naturally occurring alkaline soils.

4 Claims, No Drawings

SOIL TREATING METHOD AND COMPOSITION FOR CONSERVING NITROGEN IN NATURALLY ALKALINE SOIL

BACKGROUND OF THE INVENTION

The majority of plants obtain most or all of their nitrogen requirements from the soil. The adequate provision of nutrient nitrogen in soil for plant growth is one of the foremost agronomic problems. The nitrogen in the soil is found to occur primarily in three forms: organic nitrogen, ammonium nitrogen and nitrate nitrogen, of which ammonium nitrogen and nitrate nitrogen are the primary forms utilized by plants. This nitrogen is absorbed by plants in solution from the soil in the form of ammonium ions and nitrate ions.

The ammonium nitrogen in the soil occurs principally as colloidal-bound nitrogen, only very small quantities of the ammonium form of soil nitrogen are lost from the feeding zone of the plants by leaching.

The nitrate nitrogen in the soil is derived from the oxidation or nitrification of ammonium nitrogen by soil bacteria or by the addition of inorganic nitrate fertilizers such as ammonium nitrate, sodium nitrate, potassium nitrate and calcium nitrate. The inorganic nitrate compounds are readily soluble in water and the aqueous soil medium. When so dissolved, the nitrate nitrogen largely exists as the nitrate ion.

The nitrogen contained in the nitrate, in contrast to ammonium nitrogen, is not adsorbed by the sorption sites of the soil. A further discussion of the nature of this nitrogen problem in agriculture is set forth in U.S. Pat. No. 3,135,594.

Because of the anionic nature of this nitrate ion, nitrate nitrogen is rapidly leached by rainfall and irrigation and readily lost from the feeding zone of the plants. Further, the nitrate nitrogen is reduced by many soil bacteria to nitrogen gas. The latter process is known as denitrification and accounts for an additional loss of large quantities of nitrate nitrogen from the soil. The yearly loss from leaching and denitrification amounts to from 20 to 80 percent of the nitrate nitrogen found in the soil.

To overcome the loss of ammonium nitrogen in the soil by nitrification, it is the practice to add to the soil a nitrification inhibitor.

Representative nitrification inhibitors and their use can be found in U.S. Pat. Nos. 3,135,594, 3,494,757 and 3,635,690 and British Pat. No. 1,592,516.

While the known inhibitors are effective in reducing nitrification in naturally alkaline soils (soils with a pH of from about 7 to about 9 for short periods of time they, for the most part, do not have the prolonged activity needed for effective commercial use in such alkaline soils. Hence, there is a need for nitrification inhibitors which have prolonged activity for use in alkaline soils.

SUMMARY OF THE INVENTION

The present invention is directed to methods and compositions useful in crop culture, and is particularly concerned with new agronomical practices and compositions for conserving nitrogen in alkaline soil over a prolonged time period by suppressing the nitrification of ammonium nitrogen therein. The active agent of the compositions employed in such methods is the novel compound 4-fluoro-3- methylpyrazole corresponding to the formula

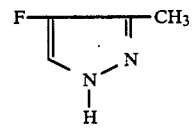

The method of the present invention comprises applying to an alkaline soil (having a pH of 7 or above) a composition which contains, as the active nitrification inhibitor, 4-fluoro-3-methylpyrazole. A further feature of the method of the present invention is that the pyrazole compound in admixture with a reduced nitrogen fertilizer can be applied to the surface of soil and subsequent irrigation or rainfall can distribute the pyrazole compound throughout the soil.

The expression "alkaline soil" is employed herein in its broadest sense to be inclusive of all conventional "soils", as defined in Webster's New International Dictionary, Second Edition, unabridged, published in 1937, G. C. Merriam Co., Springfield, Mass. which have a pH of 7 or above. Thus, the term refers to any substance or medium in which plants may take root and grow, and is intended to include not only earth, but also compost, manure, muck, sand, synthetic growth mediums such as vermiculite and pearlite and the like, adapted to support plant growth.

By the practice of this invention, the nitrification of ammonium nitrogen in the alkaline soil to nitrate nitrogen is suppressed, thereby preventing the rapid loss of ammonium nitrogen from the soil. Furthermore, by proper distribution of the pyrazole compound this action of inhibiting the transformation of ammonium nitrogen to nitrate nitrogen is effective over a prolonged period of time of at least three weeks. The ammonium nitrogen may arise from added ammonium nitrogen fertilizers or be formed in the soil by conversion of the organic nitrogen constituents found in soil or added thereto as components of organic fertilizers.

The expression "reduced nitrogen fertilizers" as employed in the present specification and claims, is understood in the art, as embracing both inorganic and organic nitrogenous materials containing nitrogen in the reduced state. Examples of known reduced nitrogen fertilizers include anhydrous ammonia, aqueous ammonia, inorganic ammonium salts such as ammonium phosphate, ammonium nitrate and ammonium sulfate, ammonium salts of organic acids, urea, cyanamide, guanidine nitrate, dicyandiamide, thiourea, urea-form and other nitrogen-containing organic chemical fertilizers as well as protein mixtures, animal tankages, green manure, fish products, crop residues, and other natural materials known to be sources of ammonium ions in soil.

The application of an effective, nitrification inhibiting, dosage of the pyrazole compound to the alkaline soil is essential for the practice of the present invention. In general, good results are obtained when the pyrazole compound is applied in the amount of from about 0.05 to about 10.0 pounds per acre of soil. The preferred amounts to be employed are dependent upon the particular situation. Thus, in determining the amount to be employed, consideration is necessary as to the soil pH, soil organic matter, temperature, soil type and time of application. By dispersing very large dosages to soil, a prolonged inhibition of nitrification can be obtained over a period of many months. The concentration of the active pyrazole compound is eventually reduced to a minimum by decomposition in the soil.

In one method for carrying out the present invention, the pyrazole compound is distributed to the soil in a broadcast application such as by spraying, dusting, distributing in irrigation water, etc. In such application, the pyrazole compound is supplied in amounts of from about 0.05 to about 10.0 pounds per acre.

In another method for carrying out the present invention, the pyrazole compound is administered to the soil in a band or row application. In such application, administration is made with or without carrier in amounts sufficient to supply to the soil a concentration of the pyrazole compound which can be as high as 10 pounds per acre or more.

In one embodiment of the present invention, the pyrazole compound is distributed throughout the soil prior to seeding or transplanting the desired crop plant.

In another embodiment, the soil in the root zone of growing plants is treated with the pyrazole compound in an amount effective to inhibit nitrification but sublethal to plant growth.

In a further embodiment, the pyrazole compound can be applied following harvest or after fallowing to prevent rapid loss of ammonium nitrogen and to build up the ammonium nitrogen formed by conversion of organic nitrogen compounds. Such practice conserves the soil nitrogen for the following growing season. In such application the upper limit is primarily an economic consideration.

Additionally, the pyrazole compound can be applied prior to, subsequent to or simultaneous with the application of a reduced nitrogen fertilizer. Such practice prevents the rapid loss of the ammonium nitrogen added as fertilizer and the ammonium nitrogen formed from the organic reduced nitrogen in fertilizers by the action of soil bacteria. In a preferred procedure, the pyrazole compound is employed as a solid or liquid composition comprising a reduced nitrogen fertilizer in intimate admixture with the pyrazole compound.

As indicated above, the present method embraces distributing the pyrazole compound as a constituent in liquid or solid fertilizer compositions. In such practice, the pyrazole compound is admixed with the fertilizer and such mixture can be modified with one or more additaments or soil treating adjuvants to formulate the mixtures employing conventional procedures as wettable powders, emulsifiable concentrates, dust, granular formulations or oil or water flowable emulsion concentrates. In preparing such formulations, the pyrazole compound/fertilizer mixture is extended with adjuvants including water, petroleum distillates or other liquid carriers, surface-active dispersing agents and inert finely-divided solids. Preferred adjuvants are surface-active dispersing agents and inert finely-divided solids; these adjuvants cooperate with the pyrazole compound so as to facilitate the practice of the present invention and to obtain an improved result. These compositions may also contain as additional adjuvants one or more other biologically active materials such as herbicides, insecticides, fungicides, miticides, bactericides, nematocides, and the like. The only requirement for these added materials is that they be both chemically and biologically compatible with the pyrazole compound.

The concentration of the pyrazole compound in the compositions can vary considerably provided the required nitrification inhibition dosage of the effective agent is supplied to the soil. In general, good results are obtained when employing liquid compositions containing from about 0.05 to about 5.0 percent by weight of the pyrazole compound; in some operations, however, compositions containing amounts of pyrazole compound in excess of 5.0 percent, such as from 5 to 98 percent of the active pyrazole compound by weight of composition are conveniently employed as, for example, in row or band application. With solids, good results are usually obtained with compositions containing from 0.05 to 5.0 percent or more by weight of pyrazole compound. In some circumstances, such as in high-intensity application, however, it is preferred to employ solid compositions containing as much as from 5 to 98 percent or more by weight of the pyrazole compound. Liquid or solid compositions in which the pyrazole compound is present in higher concentration can be utilized as such or can be employed as concentrate compositions to be diluted to prepare actual treating compositions.

The liquid compositions containing active agent, i.e., the pyrazole compound, can be prepared by admixing one or more of the active agents with water or an organic solvent, with or without the aid of a suitable surface-active dispersing agent or emulsifying agent, and admixing this mixture in an aqueous solution of the desired fertilizer.

Suitable organic solvents include acetone, diisobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the growth media.

Dispersing and emulsifying agents which can be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from 1 to 20 percent by weight of the pyrazole compound.

Solid compositions containing the active agent can be prepared by admixing the pyrazole compound, dispersed in a volatile organic solvent, with the solid fertilizer. In another procedure, the solid fertilizer can be mechanically ground with a dispersion of the pyrazole compound in a solvent and the resulting mixture prilled, granulated or otherwise formed into the desired form. After coating the solvent is vaporized off. In an additional procedure, solid granules of the fertilizer are treated with a sticking agent such as mineral oil and then coated with a dispersion of the pyrazole compound in a solvent.

These solid compositions may, if desired, also contain an alkyl aryl sulfonate or other surface-active dispersing agent. Depending upon the proportions of ingredients, these compositions can be employed without further modification or be considered as concentrates and subsequently further diluted with conventional solid carriers such as talc, chalk, gypsum, clays, or the like to obtain the desired treating composition. Furthermore, such concentrate compositions can be dispersed in water with or without added dispersing agent or agents to prepare aqueous soil treating compositions.

In these fertilizer compositions, it is desirable that the pyrazole compound be present in an amount of at least about 0.05 percent by weight based on the weight of the nitrogen present in the fertilizer as reduced nitrogen and can be present in amounts as high as 95 percent by weight of the reduced nitrogen in the fertilizer. Generally, though, amounts of pyrazole compound in excess of about 5.0 percent yield no greater advantage and are therefore seldom used. Thus, when a fertilizer composition contains both reduced nitrogen and other forms of nitrogen, such as in the case of ammonium nitrate fertilizer compositions, the amount of pyrazole compound is based on the weight of nitrogen present in the ammonium component.

The novel active 4-fluoro-3-methylpyrazole employed in the practice of the present invention is broadly but not specifically taught in Japanese Patent Publications 39-13030/1964 and 47-47183/1972 and German Pat. No. 1,592,516.

The following examples illustrate the invention but should not be construed as limiting the scope of the invention.

EXAMPLE I

4-Fluoro-3-methylpyrazole

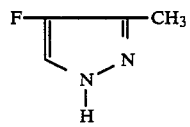

Under ambient pressure conditions, a solution was prepared by dissolving 14 grams (g) of 3-methyl-4-aminopyrazole in about 150 milliliters of 50 percent $HBF_4$ in water. This solution was cooled to 0° C. and a concentrated solution of 12 grams of $NaNO_2$ was slowly added while maintaining the temperature less than 5° C. The solution was then irradiated with a 200 watt Hanovia mercury arc lamp in an arc glass photoreactor in a water jacket at room temperature for 24 hours. The reaction mixture was cooled and sufficient 50 percent NaOH was added to obtain a pH of 8. The mixture was extracted three times with ether to obtain about 4 g of a crude oil (nuclear magnetic resonance spectroscopy indicated 80:20 4-fluoro-3-methylpyrazole:3-methylpyrazole). The aqueous phase was extracted three times with ether to obtain 0.8 g of a 50:50 4-fluoro-3-methylpyrazole:3-methylpyrazole mixture. Both fractions were dissolved in acetone and the components separated using preparative scale liquid chromatography eluting with 3:2 hexane:acetone. About 3 g of an oil was obtained which crystallized upon standing. Recrystallization from a 1:4 ether:pentane mixture yielded 2.5 g of the desired compound as near white crystal melting at 47–48° C.

Elemental Analysis

|  | % C | % H | % N |
| --- | --- | --- | --- |
| Calculated for $C_4H_5FN_2$ | 47.99 | 5.03 | 27.99 |
| Found: | 46.51 | 4.82 | 28.94 |

EXAMPLE II

Aqueous ammonium fertilizer compositions containing a predetermined amount of nitrogen, by weight, and a sufficient amount of 4-fluoro-3-methylpyrazole, dispersed in a predetermined amount of water, to give compositions containing 0.015, 0.03, 0.063, 0.125, 0.25, 0.5, 1.0 and 2.0 parts by weight of the pyrazole compound per million parts of the soil were prepared by dispersing the pyrazole compound in a predetermined amount of an aqueous fertilized solution.

The compositions so prepared were employed to treat various predetermined soils having a pH of from 7.2 to 7.8. The soil was in containers which admitted of being sealed to prevent loss of moisture. In the treating operation, the amount of the composition employed was sufficient to bring the soil moisture to ⅓ bar and the soil thoroughly mixed to insure a substantially uniform distribution of the composition throughout the soil.

In a check operation, other soils similarly prepared were fertilized with a similar aqueous fertilizer composition containing the same amount of water but no pyrazole compound. The composition was applied in an amount to supply the same concentration of nitrogen to the soil as the treating composition containing the compound. All of the containers were then sealed and maintained at about 80° F. for a predetermined number of days.

At the end of the time period, the extent of nitrification of the added fertilizer was determined by analysis for ammonium nitrogen. The analysis was carried out using an ammonium electrode. The results of this analysis and the compounds tested, the fertilizer used and the number of test days are set forth below in Table I.

TABLE I

| Soil type | Soil pH | Fertilizer | Days After Treatment | Amount of Ammonium Nitrogen Applied To Soil in ppm | Percent Ammonium Nitrogen Remaining at Indicated Treating Rate of 4-fluoro-3-methylpyrazole | | | | | |
| --- | --- | --- | --- | --- | --- | --- | --- | --- | --- | --- |
| | | | | | 1.0 | 0.5 | 0.25 | 0.125 | 0.063 | Control |
| Muscatine | 7.2 | Urea | 14 | 250 | 77 | — | 72 | — | 27 | 6 |
| Muscatine | 7.2 | Urea | 25 | 250 | 66 | — | 60 | — | 5 | 5 |
| Hoytville Clay | 7.2 | Urea | 14 | 250 | 76 | — | 74 | — | 13 | 7 |
| Hoytville Clay | 7.2 | Urea | 25 | 250 | 66 | — | 52 | — | 7 | 4 |
| Catlin Clay | 7.3 | Urea | 14 | 250 | 91 | — | 91 | — | 59 | 19 |
| Catlin Clay | 7.3 | Urea | 23 | 250 | 91 | — | 86 | — | 23 | 4 |
| Zamora | 7.5 | Urea | 14 | 250 | 76 | — | 73 | — | 23 | 10 |
| Zamora | 7.5 | Urea | 21 | 250 | 65 | — | 65 | — | 15 | 14 |
| Londo | 7.2 | DAP | 9 | 300 | 100 | 100 | 100 | 100 | — | 37 |
| Londo | 7.2 | DAP | 23 | 300 | 78 | 79 | 80 | 80 | — | 6 |
| Londo | 7.2 | DAP | 45 | 300 | 19 | 18 | 19 | 13 | — | 3 |
| Londo | 7.2 | DAP | 12 | 250 | 96 | 96 | 97 | 96 | 87 | 47 |
| Londo | 7.2 | DAP | 22 | 250 | 88 | 88 | 87 | 85 | 66 | 22 |

What is claimed is:
1. 4-Fluoro-3-methylpyrazole corresponding to the formula

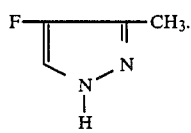

2. A composition which comprises a reduced nitrogen fertilizer in admixture with from about 0.05 to about 98 percent by weight of an active agent which is a 4-fluoro-3-methylpyrazole.

3. A method for treating naturally alkaline soil to inhibit the conversion therein of ammonium nitrogen to nitrate and nitrite nitrogen and to prevent rapid loss of ammonium nitrogen therefrom which comprises applying to said soil a nitrification suppressing amount of a composition comprising a reduced nitrogen fertilizer in admixture with from about 0.05 to about 98 percent by weight of an active agent which is 4-fluoro-3-methylpyrazole.

4. A nitrification inhibition-fertilizer composition useful for delayed incorporation into soil which comprises a reduced nitrogen fertilizer in admixture with from about 0.05 to about 98 percent of an active agent which is a 4-fluoro-3-methylpyrazole.

* * * * *